United States Patent
Jeong et al.

(10) Patent No.: US 7,783,391 B2
(45) Date of Patent: *Aug. 24, 2010

(54) APPARATUS AND METHOD FOR CONTROLLING VEHICLE BY TEETH-CLENCHING

(75) Inventors: Hyuk Jeong, Daejeon (KR); Jong Sung Kim, Daejeon (KR); Wookho Son, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 1269 days.

This patent is subject to a terminal disclaimer.

(21) Appl. No.: 11/324,884

(22) Filed: Jan. 4, 2006

(65) Prior Publication Data

US 2007/0100508 A1    May 3, 2007

(30) Foreign Application Priority Data

Oct. 28, 2005    (KR) ...................... 10-2005-0102368

(51) Int. Cl.
G09G 5/00    (2006.01)
(52) U.S. Cl. .......................................... 701/1; 600/587
(58) Field of Classification Search .................... 701/1; 600/587, 590, 595, 546, 547; 433/68, 69, 433/24
See application file for complete search history.

(56) References Cited

U.S. PATENT DOCUMENTS

| 5,212,476 A * | 5/1993 | Maloney ................ 340/825.19 |
| 6,613,001 B1 * | 9/2003 | Dworkin .................... 600/590 |
| 6,961,623 B2 | 11/2005 | Prochazka |
| 2006/0061544 A1 * | 3/2006 | Min et al. .................. 345/156 |

FOREIGN PATENT DOCUMENTS

| KR | 10-20050081995 | 8/2005 |
| WO | WO 9922417 | 5/1999 |

* cited by examiner

*Primary Examiner*—Dalena Tran
(74) *Attorney, Agent, or Firm*—Ladas & Parry LLP (57) ABSTRACT

An apparatus and method for controlling vehicle by teeth clenching are provided. The apparatus includes: an electromyogram signal obtaining unit including electromyogram sensors disposed at both sides for generating an electromyogram signal according to a predetermined muscle moved when a disabled person clenches teeth, and a ground electrode connected to a body of the disabled persons for providing a reference voltage; and a vehicle driving unit including a control command generating unit for generating a vehicle driving command according to the electromyogram signal by classifying the electromyogram signal based on a side of teeth clenched, a duration time for clenching teeth and a sequence of teeth clenching motions made by the disabled person, a control command interface for generating a predetermined level of voltage according to the created vehicle driving command, and a vehicle driving unit for driving the vehicle according to the generated voltage.

21 Claims, 6 Drawing Sheets

APPARATUS AND METHOD FOR CONTROLLING VEHICLE BY TEETH-CLENCHING

BACKGROUND OF THE INVENTION

1. Field of the Invention

The present invention relates to an apparatus and method for controlling a vehicle by teeth-clenching, and more particularly, to an apparatus and method for controlling a vehicle according to electromyogram generated from a temporalis muscle when a quadriplegic disabled person clenches teeth.

2. Description of the Related Art

Disabled persons have various types of impairments. Generally, a person suffered by spinal cord damage is a quadriplegia which means a person paralyzes all four limbs. Various vehicles and driving method thereof were introduced for quadriplegic disabled persons. For example, an electric wheelchair and various driving methods thereof were introduced.

As a conventional method of controlling an electric wheelchair for a quadriplegic disabled person, a joy stick based controlling method and a sip-puff based controlling method were introduced. According to the joy stick based controlling method, a disabled person is allowed to control the electric wheelchair by arranging a joy stick under the jaw and moving the joy stick using the jaw. However, the disabled person may have suffering from his neck because the disable person consistently controls the joy stick through moving his neck while driving the electric wheelchair. Also, the sight of disabled person is limited because he must hold his neck while controlling the electric wheelchair in one direction. Therefore, the method of controlling the electric wheelchair using the joy stick has a safety problem. According to the sip-puff based controlling method, a disabled person controls the electric wheelchair by inhaling or exhaling air through a breath controlling device having a shape of straw. The sip-puff controlling method is not good for the disabled person in a view of sanitary because the disabled person must bite the breath controlling device. Also, the look of controlling the electric wheelchair is not enjoyable. In particular, the disabled person needs to learn how to control the electric wheelchair with the breath controlling device and it requires plenty of time to be familiar since it is not intuitive to control the electric wheelchair.

Hereinafter, shortcomings of conventional apparatuses and methods for controlling a vehicle for a disabled person will be described.

A first conventional method of controlling the vehicle for disabled persons by moving shoulder was introduced in Korea Patent Application No. 10-2003-00118856. In the conventional method using the shoulder, a driving control device is disposed at a coat or a jacket of a disabled person having spinal cord impairment and the disabled person controls the electric wheelchair by moving his shoulder. That is, the driving control device senses a moving direction and a level of the shoulder and controls the electric wheelchair according to the sensed movements of the shoulder. However, such a conventional method cannot be applied for a disabled person cannot move his shoulder. Also, the disabled person may have suffering of his shoulder because the disabled person must lift up the shoulder while driving the electric wheelchair in a forward direction.

A second conventional method of controlling the vehicle for disabled person was disclosed in Korea Patent Application No. 10-2003-0005471 entitled "ELECTRIC WHEELCHAIR INTERFACE DEVICE AND METHOD USING ELECTROMYOGRAM SIGNAL AND ELECTRIC WHEELCHAIR." The second conventional method obtains the electromyogram signal generated from a sternocleidomastoid muscle and a trapezius muscle when a disabled person moves his neck and controls the electric wheelchair according to the obtained electromyogram signal. In order to use the second conventional method, the disabled person must wear a sensor for obtaining the electromyogram signal on his neck. Therefore, the disabled person may be uncomfortable and have suffering of his neck since the disabled person consistently moves his neck to control the electric wheelchair.

A third conventional method of controlling the vehicle using a head-band type sensor and a bite switch for disabled person was disclosed in Korea Patent Application No. 10-2003-0088730. In order to use the third conventional method, a disabled person must wear a head-band type slope detecting sensor on his head to sense a direction and an angle of tilted head and holds a bite switch in his mouth to drive the electric wheelchair. Such a bite switch makes the disabled person uncomfortable.

SUMMARY OF THE INVENTION

Accordingly, the present invention is directed to an apparatus and method for controlling a vehicle by teeth clenching, which substantially obviates one or more problems due to limitations and disadvantages of the related art.

It is an object of the present invention to provide an apparatus for controlling a vehicle such as an electric wheelchair by teeth clenching, which is designed as a headgear such as a hat or a hair-band, by sensing and analyzing electromyogram signal generated by a teeth clenching motion of the disabled person, distinguishing the teeth clenching motion of the disabled person into a left side teeth clenching motion, a right side teeth clenching motion, a both side teeth clenching motion and driving the vehicle according to the distinguished teeth clenching motion and a duration time for clenching the teeth so as to allow the disabled person to intuitive control the vehicle and to minimize discomfort when the disable person wears the vehicle driving apparatus.

It is another object of the present invention to provide a method of controlling a vehicle based on teeth clenching Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, there is provided an apparatus for controlling a vehicle by a teeth clenching motion made by a user including: an electromyogram signal obtaining unit including electromyogram sensors disposed at both sides for generating an electromyogram signal according to a predetermined muscle moved when a disabled person clenches teeth, and a ground electrode connected to a body of the disabled persons for providing a reference voltage ; and a vehicle driving unit including a control command generating unit for generating a vehicle driving command according to the electromyogram signal by classifying the electromyogram signal based on a side of teeth clenched, a duration time for clenching teeth and a sequence of teeth clenching motions made by the disabled person, a control command interface for generating a predetermined level of voltage according to the created vehicle driving command, and a vehicle driving unit for driving the vehicle according to the generated voltage.

In another aspect of the present invention, there is provided a method for controlling a vehicle by a teeth clenching motion including the steps of a) sensing an electromyogram signal of a predetermined muscle moved by a teeth clenching motion made by a user; b) generating a vehicle driving command according to the sensed electromyogram signal by classifying the sensed electromyogram signal based on a side of teeth clenched, a duration time for clenching teeth and a sequence of teeth clenching motions made by the user at a control command generating unit; c) generating a predetermined level of voltage according to the created vehicle driving command; and d) driving the vehicle according to the generated voltage.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention, are incorporated in and constitute a part of this application, illustrate embodiments of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings.

A vehicle controlling apparatus according to the present invention control a vehicle according to a teeth clenching motion made by a user. The teeth clenching motion can be made by a disabled person having serious impairment by distinguishing a right teeth clenching motion, a left teeth clenching motion and a both side teeth clenching motion. A muscle used for clenching teeth is a masseter muscle around a jaw and a temporalis muscle at a temple. Since the masseter muscle is located at both side of jaw, it is not easy to attaché sensors around the masseter muscle. Although the sensor is attached at the masseter muscle, a user may be uncomfortable. In the present invention, the sensors are attached around temples of side head to obtain an electromyogram signal from the temporalis muscle. Since the sensors are disposed at a headgear such as a hair band or a hat, it minimizes discomfort of user and maximizes convenience.

Figure 1:
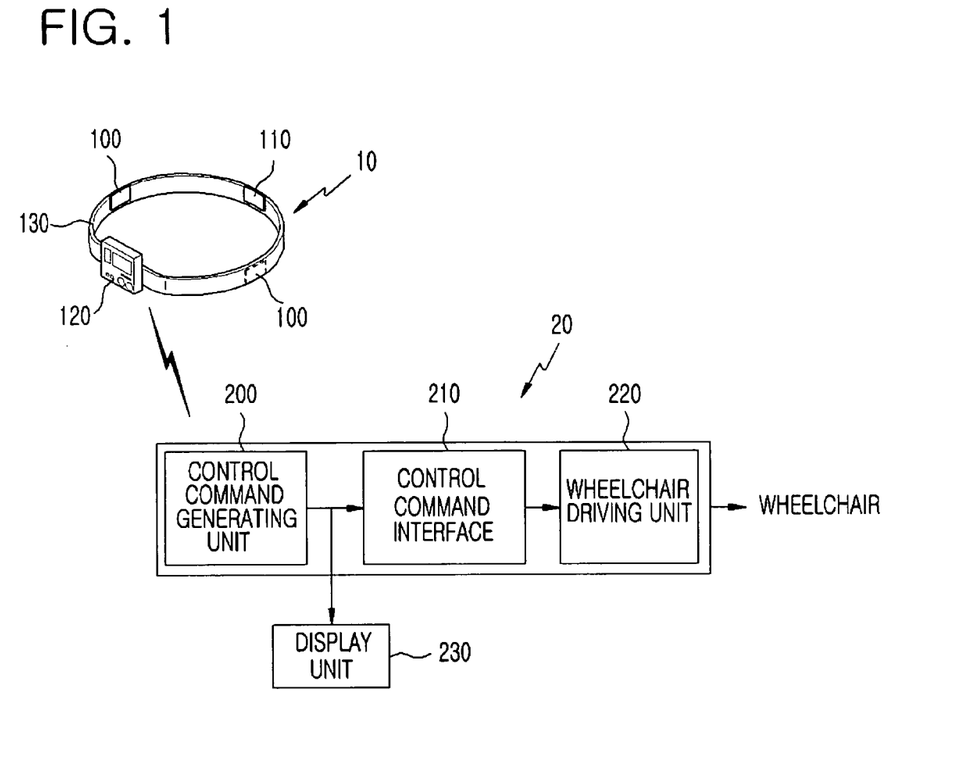
FIG. 1 is a conceptual view illustrating an apparatus for controlling a vehicle by teeth clenching according to an embodiment of the present invention.

FIG. 1 is a conceptual view illustrating an apparatus for controlling a vehicle by teeth clenching according to an embodiment of the present invention. As an embodiment of the present invention, the vehicle controlling apparatus has a shape of a hair-band.

As shown in FIG. 1, the vehicle controlling apparatus according to the present embodiment includes a signal obtaining and transmitting unit 10 for obtaining an electromyogram signal and a signal processing unit 20 for processing the obtained electromyogram signals.

The signal obtaining and transmitting unit 10 includes two electromyogram sensors 100 for sensing electromyogram signals generated from a temporalis muscle when a teeth clenching motion made by a disabled person; a ground electrode 110 for measuring a reference voltage; and an amplifying and transmitting unit 120 for amplifying the sensed signal, transforming the amplified signal to a digital signal and transmitting the digital signal in wireless link.

The electromyogram sensors 100, the ground electrode 110 and the amplifying and transmitting unit 120 are disposed in a hair-band 130. It is preferable to design the hair-band 130 to be easily wearable according to ability of the disabled person. For example, Velcro is attached at an inside surface of the hair-band 130 to easily adjust a position of the electromyogram sensors 100 corresponding to conditions of a disabled person such as a shape of a head in order to accurately sense the electromyogram signal. In the present embodiment, the signal obtaining and transmitting unit 10 is disposed in the hair-band 130. However, the signal obtaining and transmitting unit 10 may be disposed in various types of headgears such as a hat or a cap.

The electromyogram sensor 100 uses voltage difference between two pairs of electrodes to obtain the electromyogram generated by the teeth clenching motion of the disabled person so as to secure a safety against an eye blanking motion and to minimize influence of electroencephalogram transferred from a brain. In the present embodiment, two sensors 100 are included. However, the present invention is not limited by the number of the electromyogram sensors.

The signal processing unit 20 includes a control command generating unit 200, a control command interface 210 and a wheelchair driving unit 220.

The control command generating unit 200 receives an electromyogram signal transmitted through a wireless link, processes the received signal and generates a command to drive the wheelchair. The control command interface 210 transfers the generated command to the wheelchair driving unit 220 by transforming the generated command suitable form the wheelchair driving unit 220. The wheelchair driving unit 220 controls driving devices such as a left motor and/or a right motor according to the generated command to drive the wheelchair.

In the present embodiment, the signal obtaining and transmitting unit 10 and the signal processing unit 20 communicate one another through a wireless communication link. However, they may communicate through a wired link.

Also, the apparatus for controlling a vehicle by teeth clenching according to the present embodiment may further include a display unit 230 to display the generated command and information thereof.

Figure 2:
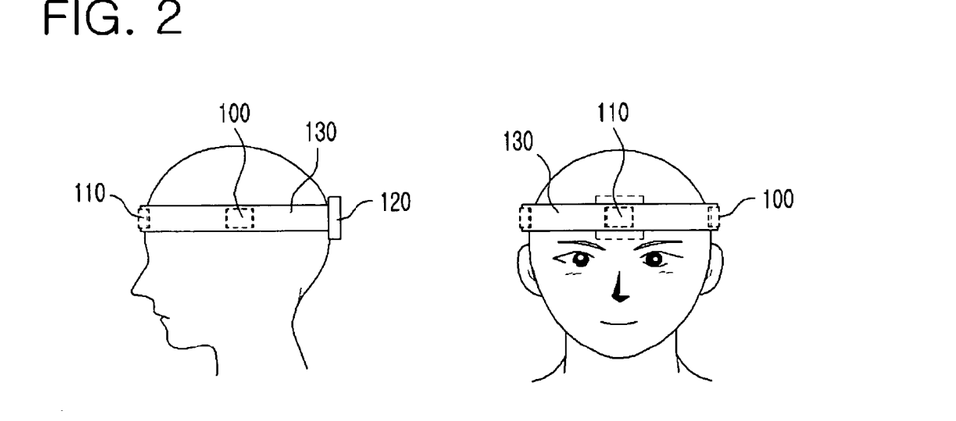
FIG. 2 is a view depicting a disabled person wearing the vehicle controlling apparatus shown in FIG. 2.

FIG. 2 is a view showing a disabled person wearing the apparatus for controlling a vehicle by teeth clenching shown in FIG. 1.

Referring to FIG. 2, the electromyogram sensors 100 and the ground electrode 110 are disposes inside of the hair-band 30 in parallel at proper positions so that the ground electrode 110 is arranged at a center of a forehead of a disabled person and the electromyogram sensors 100 are arranged at both side heads of the disabled person when the disabled person wears the hair-band 30. Since the electromyogram signal generated by the teeth clenching motion is easily detected around temples that are about 10 cm apart from an end of eyebrow formed on the temporalis muscle, the disabled person adjusts the hair-band to arrange the electromyogram sensors 100 around the temples after wearing the hair-band 30.

Hereinafter, a method of controlling a vehicle by teeth clenching according to the present invention will be described with reference to accompanying drawings.

Figure 3:
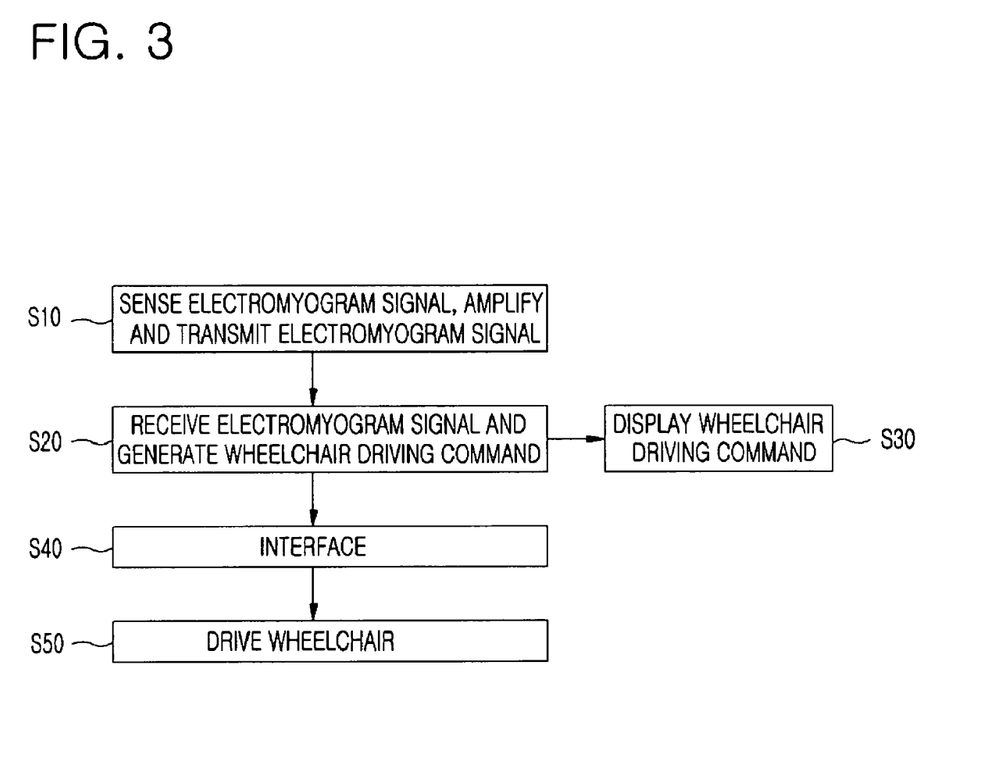
FIG. 3 is a flowchart showing a method for controlling a vehicle by teeth clenching according to an embodiment of the present invention.

FIG. 3 is a flowchart of a method for controlling a vehicle by teeth clenching according to an embodiment of the present invention.

Referring to FIG. 3, the electromyogram sensors 100 senses the electromyogram signal generated from the temporalis muscle when a user makes a teeth clenching motion. Then, the amplifying and transmitting unit 120 amplifies the sensed electromyogram signal, transforms the amplified signal to a digital signal and transmits the digital signal through a wireless link at step S10.

The control command generating unit 200 receives the transmitted signal from the signal obtaining and transmitting unit 10 and generates a command to control the wheelchair by processing the received signal at step S20. Herein, the generated wheelchair control command is displayed on the display unit 230 at step S30 and the control command interface 210 transfers the wheelchair control command to the wheelchair driving unit 220 at step S40. The wheelchair driving unit 220 drives the left motor or the right motor according to the wheelchair control command at step S50.

Figure 4:
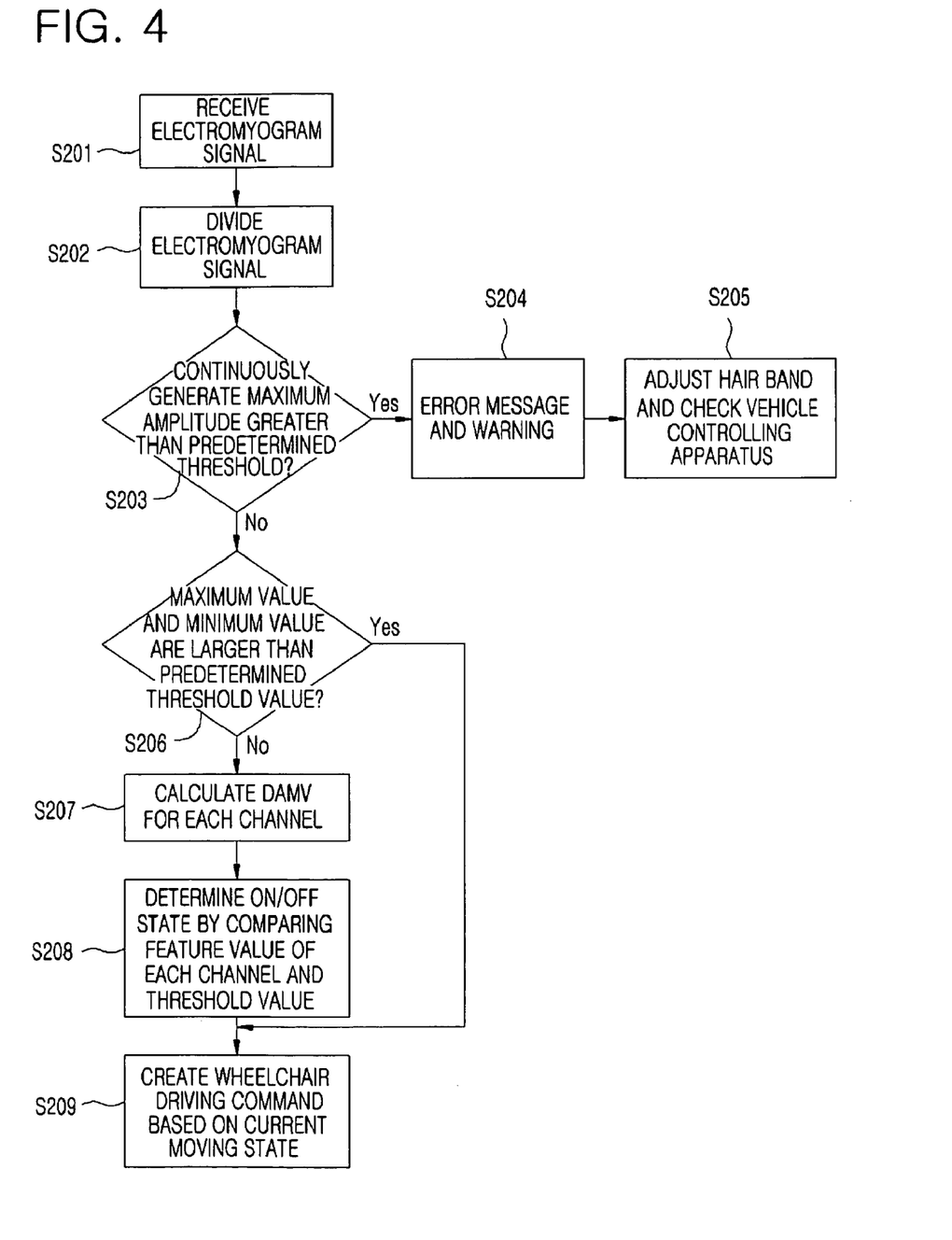
FIG. 4 is a flowchart showing a method of processing a signal transmitted from the vehicle controlling apparatus according to an embodiment of the present invention.

FIG. 4 shows a method of processing a signal transmitted from the vehicle controlling apparatus according to an embodiment of the present invention. That is, the flowchart shown in FIG. 4 describes the step S20 shown in FIG. 3 in detail.

Referring to FIG. 4, the signal processing unit 20 receives the electromyogram signal from the signal obtaining and transmitting unit 10 at step S210. Since the signal obtaining and transmitting unit 10 and the signal processing unit 20 communicate one another based on a short range wireless communication scheme, a Bluetooth protocol consuming comparatively less power may be used.

The received signal is processed through a preprocessing step. In the preprocessing step, the electromyogram signals inputted from two channels, i.e., a left channel and a right channel, are divided by 100 ms at step S202 because electromyogram signals longer than 100 ms can be assumed as stationary. However, the length of the divided electromyogram signal may vary according to it's condition. While transforming the electromyogram signal to a digital signal, about 1 kHz of sampling frequency is used. Therefore, 100 samples are obtained from each of the divided electromyogram signals.

The preprocessing step includes a step for detecting poor contacts of the electromyogram sensor 100 or the ground electrode 110 and generating the wheelchair driving command based on the detected poor contacts. The poor contacts maximize the amplitude of the electromyogram signal as a square wave. Accordingly, the signal processing unit 20 observes the electromyogram signals whether the maximum amplitudes greater than a predetermined threshold value are continuously generated or not at step S203. If the maximum amplitudes are continuously generated, the vehicle controlling apparatus according to the present invention notices the error of detecting the electromyogram signal to the user by creating an error message or reproducing a predetermined sound at step S204. Then, the user adjusts the hair-band, or the vehicle controlling apparatus is checked at step S205.

After the step S203, a minimum value and a maximum value of the electromyogram signal are compared to a minimum threshold value and a maximum threshold value and frequency of the minimum and the maximum values identical to the minimum and the maximum threshold value is calculated at step S206. If the frequency is greater than a predetermined frequency, the wheelchair driving command for stopping the wheelchair is generated at step S209 without performing a step for extracting features from the electromyogram signal. According to the stopping command, the wheelchair stops or is maintained as a stop state.

After the preprocessing step, features are extracted from the electromyogram signals at step S207. That is, a difference of absolute mean values is extracted from electromyogram signals obtained from two channels based on following equation.

$$DAMV = \frac{1}{N-1} \sum_{i=2}^{N} |x(i) - x(i-1)|$$

Herein, N denotes the number of samples in each of the divided electromyogram signals and x(i) represents the digital electromyogram signal value at an index i. Since the DAMV represents the characteristics of electromyogram signal which is rapidly changed and does not include direct current (DC) components, it does not require a step for eliminating the DC components.

Using the DAMV value, a pattern classification is performed at step S208. In the pattern classification, the feature values of electromyogram signals from two channels are compared with a predetermined threshold value. If the feature value is greater than the predetermined threshold value, the electromyogram signal from corresponding channel is classified into an ON state. On the contrary, if the feature value is smaller than the predetermined threshold value, the electromyogram signal is classified into an OFF state. That is, the electromyogram signals obtained from two channels are classified into four different state signals such as 1) the electromyogram signals from a first and a second channel are OFF states; 2) the electromyogram signal obtained from a first channel arranged at a left temple is the ON state and the electromyogram signal obtained from a second channel arranged at a right temple is the OFF state; 3) the electromyogram signal obtained from the first channel is the OFF state and the electromyogram signal obtained from the second channel is the ON state; and 4) the electromyogram signals obtained from the first and the second channels are both ON states. Such classified patterns are defined as REST, LEFT, RIGHT and BOTH. As described above, four basic commands can be created based on electromyogram signals from two channels.

Then, a command for driving a wheelchair is generated using the defined pattern in the pattern classifying step. Although the defined four basic commands may be used to control the wheelchair, more commands are required to smoothly and finely control the wheelchair such as to move the wheelchair in a reverse direction and to turn the wheelchair to a right or a left side while driving in a forward direction. Therefore, various commands are created according to previous moving directions of wheelchair and a history of recognizing basic patterns in the present embodiment. Such a method of creating the various commands is shown in FIGS. 5A to 5D.

FIGS. 5A to 5D are flowcharts of a method of controlling an electric wheelchair according to an embodiment of the present invention.

FIGS. 5A through 5D shows steps for creating various commands to drive the wheelchair based on the basic patterns such as REST, LEFT, RIGHT and BOTH. Hereinafter, definitions of commands shown in FIGS. 5A to 5D will be described at first.

Pat is a variable denoting a currently recognized basic teeth-clenching pattern or a switch. The Pat has one of values of REST, LEFT (L), RIGHT (R) and BOTH.

PrePat[i] denotes a basic teeth-clenching pattern recognized at $i^{th}$ stage (i=0, 1, 2, ... n1) where n1 is a predetermined natural number that denotes a number of divided electromyogram signals of the past pattern.

Act is a variable denoting motions of the wheelchair. There are 13 wheelchair motions as follows.
 1. STOP: stop
 2. GF: move in forward direction
 3. GB: move in reverse direction
 4. TL: turn to left
 5. TR: turn to right
 6 GFL1: make a short turn to left (counterclockwise) while moving in forward direction.
 7. GFL2: make a large turn to left while moving in forward direction
 8. GFL3: make a quick turn to left while moving in forward direction. It is a command to drive the wheelchair in a narrow road bended at 90 degree.
 9. GFR1: make a short turn to right (clockwise) while moving in forward direction
 10. GFR2: make a large turn to right while moving in forward direction
 11. GFR3: make a quick turn to right while moving in forward direction.
 12. GBL1: make a left turn (counterclockwise) while moving in reverse direction
 13. GBR1: make a right turn (clockwise) while moving in reverse direction PreAct is a variable denoting a motion of the wheelchair at a previous stage.

Dir is a variable for determining whether a moving direction of wheelchair is a forward direction or a backward direction. In case of the forward direction, the Dir has a value of Forward. In case of the reverse direction, the Dir has a value of Reverse.

bCheck is a variable for determining how many times a user clenches teeth. If the user clenches teeth one time, the bCheck has a value of TRUE. If the user clenches teeth two or more times, the bCheck has a value of FALSE. The bCheck is used to change a direction of moving the wheelchair when the user clenches teeth for a predetermined time and then releases teeth two times. Herein, if the user dose not clenches and release two times, the value of bCheck is transformed to FALSE. Therefore, it prevents the wheelchair from being turned when the wheelchair is stopped for a short time.

When an initial state of driving the wheelchair, the PrePat and the PreAct are set as REST and STOP, respectively. Then, features are extracted the electromyogram signals and the patterns of electromyogram signals are classified as follows.

Figure 5A:
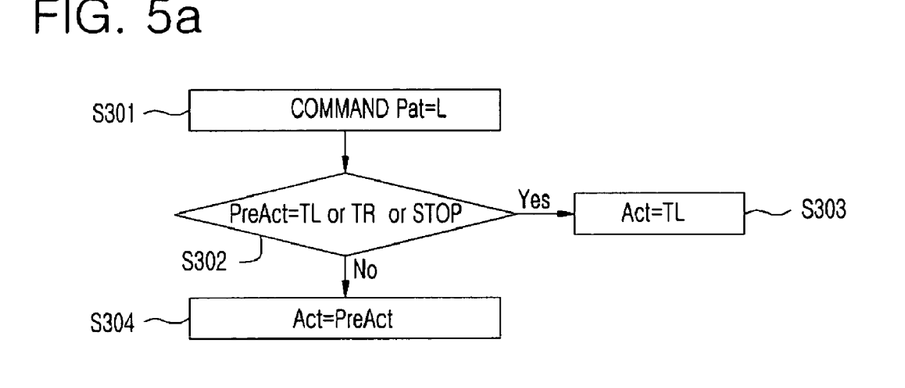
FIGS. 5A to 5D are flowcharts of a method of controlling an electric wheelchair according to an embodiment of the present invention.

FIG. 5A shows a wheelchair controlling algorithm when the pattern (Pat) is left (L). Referring to FIG. 5A, the left pattern (Pat=L) is received at step S301. Then, the previous motion (PreAct) of wheelchair is determined at step S302. If the previous motion (PreAct) is TL, TR or STOP at step S302, a wheelchair driving command is set as TL at steps S303. If the previous motion (PreAct) is not TL, TR or STOP at step S302, the motion of wheelchair (Act) is set as the previous wheelchair motion (PreAct) at step S304.

Figure 5B:
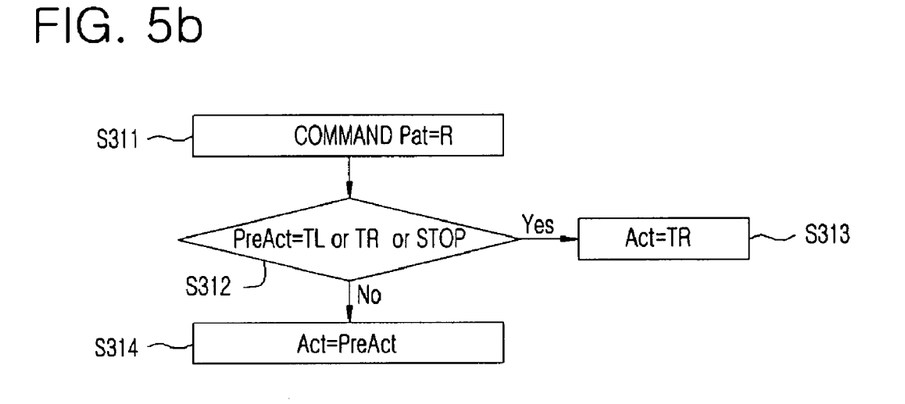

FIG. 5B shows a wheelchair controlling algorithm when the pattern Pat is a right (R). Referring to FIG. 5B, the right pattern (Pat=R) is received at step S311. Then, the previous motion (PreAct) of wheelchair is determined at step S312. If the previous motion (PreAct) is TL, TR or STOP at step S312, a wheelchair driving command is set as TR at steps S313. If the previous motion (PreAct) is not TL, TR or STOP at step S312, the motion of wheelchair (Act) is set as the previous wheelchair motion (PreAct) at step S314.

Figure 5C:
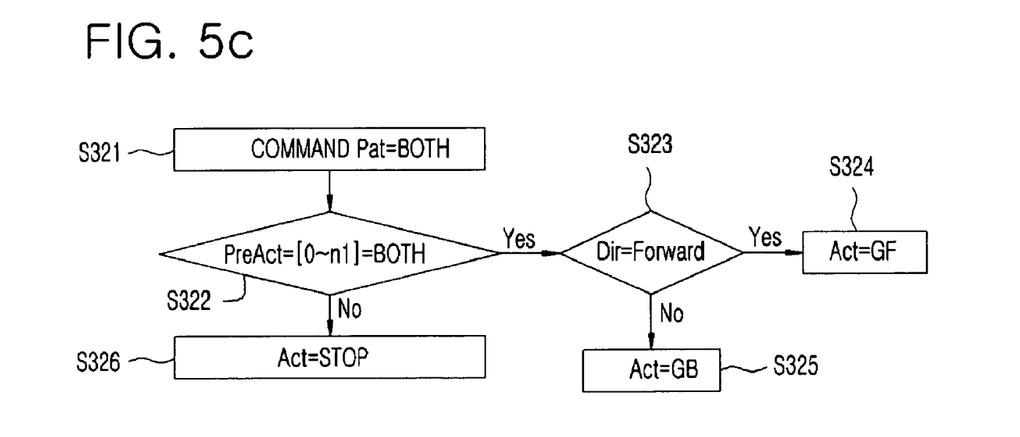

FIG. 5C shows a wheelchair controlling algorithm when the pattern (Pat) is BOTH. Referring to FIG. 5C, the BOTH pattern is received at step S321. Then, the previous motions (PreAct[0 to n1]) of wheelchair from the stage 0 to the stage n1 are determined at step S322. If the previous motions (PreAct[0 to n1]) are BOTH at step S322, it determines whether Dir is Forward or not at step S333. If the Dir is Forward at step S333, the Act of wheelchair is set as GF at steps S324. If the Dir is Backward at step S333, the Act of wheel chair is set as GB at step S325. Therefore, a user must consistently clench both side teeth for a predetermined time to move the wheelchair in the forward direction or the backward direction. By checking previous motions of wheelchair, it prevents the wheelchair from being moved when the user accidentally clenches both side teeth. If the previous motions (PreAct[0 to n1]) are not BOTH at step S322, the motion of wheelchair (Act) is set as STOP at step S326.

Figure 5D:
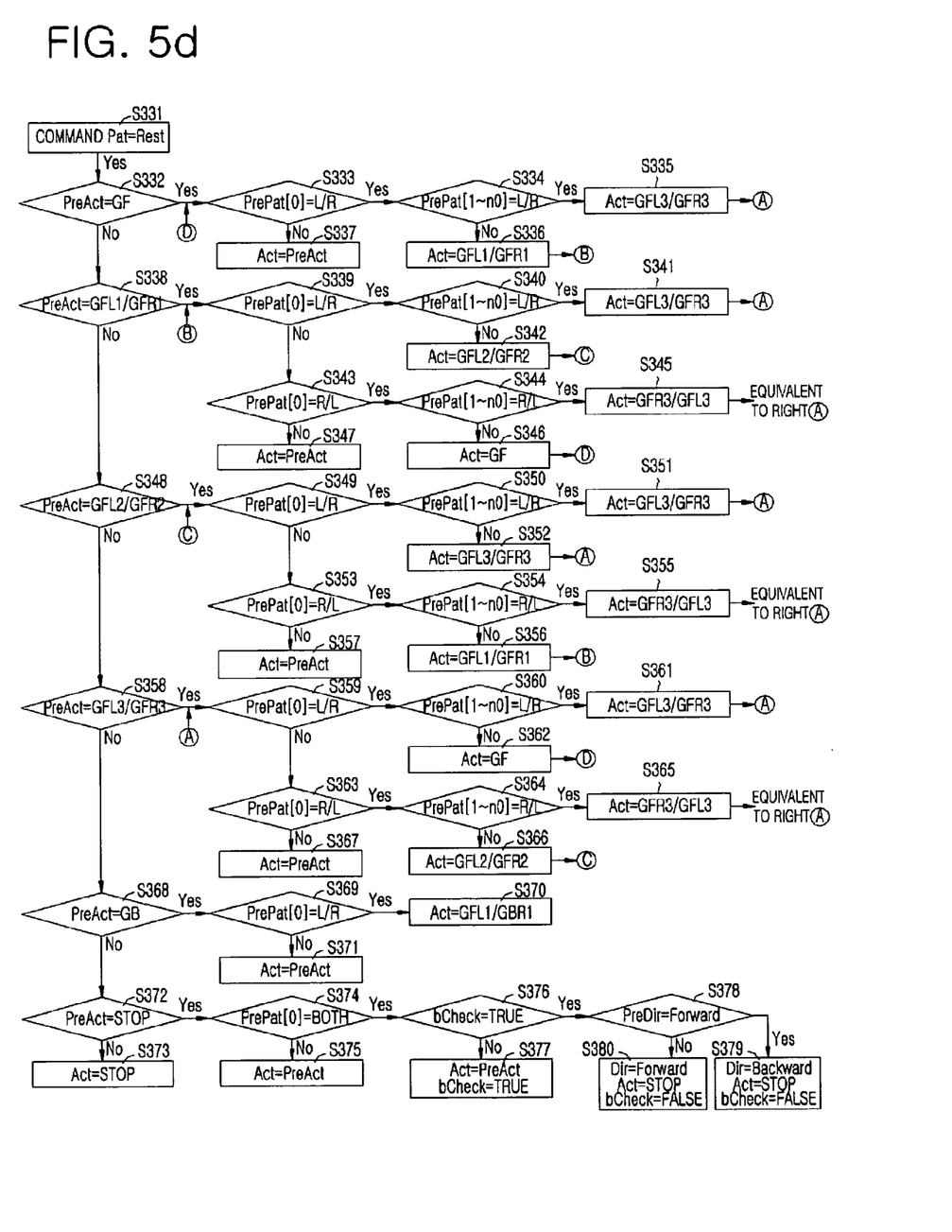

FIG. 5D shows a wheelchair controlling algorithm when the pattern (Pat) is REST.

Referring to FIG. 5D, the REST pattern (Pat=REST) is received at step S332. Then, the PreAct is checked at steps S332, S338, S348, S358, S368 and S372. If the PreAct is one of GF, GFL1, GFL2, GRF and GFR2, it denotes that the wheelchair is moving in a forward direction. In order to make turns to left or right, a user clenches a left side teeth or a right side teeth shortly. Then, the moving direction of the wheelchair is changed. In case of GF, the wheelchair turns to the right at the moment a user releases teeth after clenching a right side teeth for a predetermined time. By repeatedly clenching and releasing the right side teeth, the wheelchair turns to the right little by little. On the contrary, the wheelchair turns to the left at the moment a user release teeth after clenching a left side teeth for a predetermined time. For example, if a user releases the teeth after clenching the right or the left side teeth for a predetermined time, i.e., about 0.2 to 1 sec, the wheelchair changes a direction according to the side teeth clenched. That is, the turning level is changed sequentially through GFL2→GFL1→GF→GFR1→GFR2 or GFR2→GRF1→GF→GFL1→GFL2. If a user clenches a right or a left side teeth for a predetermined time, i.e., about 1 sec, while changing the direction, the wheelchair makes a quick turn as GFL3 or GFR3 without regarding to previous moving direction such as GF, GFL1, GFR1, GFL2 and GFR2.

In FIG. 5D, L/R or R/L denotes that reflection of command according to the flowchart at a same position. Therefore, the vehicle controlling method will be described for one of L/R.

Referring to FIG. 5D, the REST pattern is received at step S331. Then, a previous motion (PreAct) is determined at step S332: If the PreAct is GF at step S332, the previous patterns from the stage 0 to the stage n0 (PrePat[0, 1, . . . ,n0]) are determined at steps S333 and S334. If the PrePat[0] is L and PrePat[1 to n0] are L at steps S333 and S334, it determines how long a user clenches the teeth. If the user clenches the teeth longer than a predetermined time, the motion (Act) of wheelchair is set to GFL3 at step S335. If the user clenches the teeth no longer than the predetermined time, the Act is set to GFL1 a step S336. At the step S355, if PrePat[0] is not 'L', the Act is set to PreAct at step S337.

Meanwhile, if the PreAct is GFL1 at step S338 after receiving the REST pattern at step S331, the previous patterns from the stage 0 to the stage n0 (PrePat[0, 1, . . . ,n0]) are determined at steps S339 and S340. If the PrePat[0] is L and PrePat[1 to n0] are L at steps S339 and S340, it determines how long a user clenches the teeth. If the user clenches the teeth longer than a predetermined time, the motion (Act) of wheelchair is set to GFL3 at step S341. If the user clenches the teeth no longer than the predetermined time, the Act is set to GFL2 a step S342. If PrePat[0] is not L at the step S339 and if PrePat [0] is R at step S343, the PrePat [1 to n0] are determined at step S344. If the PrePat [1 to n0] are R and if the user clenches the teeth longer than the predetermined time, the Act is set to GFL3 at step S345. If not at the step S344, the Act is set to GF at step S346. Also, if PrePat[0] is not R a step S343, the Act is set to the PreAct at step S347.

If the PreAct is GFL2 at step S348 after receiving the REST pattern at step S331, the previous patterns from the stage 0 to the stage n0 (PrePat[0, 1, . . . ,n0]) are determined at steps S349 and S350. If the PrePat[0] is L and PrePat[1 to n0] are L at steps S349 and S350, it determines how long a user clenches the teeth. If the user clenches the teeth longer than a predetermined time, the motion (Act) of wheelchair is set to GFL3 at step S351. If the user clenches the teeth no longer than the predetermined time, the Act is set to GFL3 a step S352. If PrePat[0] is not L at the step S349 and if PrePat [0] is R at step S353, the PrePat [1 to n0] are determined at step S354. If the PrePat [1 to n0] are R and if the user clenches the teeth longer than the predetermined time, the Act is set to GFL3 at step S355. If not at the step S354, the Act is set to GFL1 at step S356. Also, if PrePat[0] is not R a step S353, the Act is set to the PreAct at step S357.

If the PreAct is GFL3 at step S358 after receiving the REST pattern at step S331, the previous patterns from the stage 0 to the stage n0 (PrePat[0, 1, . . . ,n0]) are determined at steps S359 and S360. If the PrePat[0] is L and PrePat[1 to n0] are L at steps S359 and S360, it determines how long a user clenches the teeth. If the user clenches the teeth longer than a predetermined time, the motion (Act) of wheelchair is set to GFL3 at step S361. If the user clenches the teeth no longer than the predetermined time, the Act is set to GF a step S362. If PrePat[0] is not L at the step S359 and if PrePat [0] is R at step S363, the PrePat [1 to n0] are determined at step S364. If the PrePat [1 to n0] are R and if the user clenches the teeth longer than the predetermined time, the Act is set to GFL3 at step S365. If not at the step S364, the Act is set to GFL2 at step S366. Also, if PrePat[0] is not R a step S363, the Act is set to the PreAct at step S367.

In FIG. 5D, it determines whether PrePat [0] is 'L' or not when PreAct is 'GF' in order to prevent the wheelchair to be turned by error. That is, the wheelchair makes turns only when patterns LEFT or RIGHT are constantly detected at least more than two blocks. Such a prevention mechanism is performed when the PreAct is GF as well as forwarding moving and backward moving of the wheelchair.

While making the quick turn shown in FIG. 5D, the wheelchair moves in the forward direction if a user clenches and releases an opposite side teeth of the turning direction.

If the PreAct is GB at step S368, the wheelchair makes a right turn or a left turn at steps S369 to S371 by clenching and releasing the right side teeth or the left side teeth, respectively. It is preferable not to provide a command for a quick turn while the wheelchair is moving in reverse direction for safety purpose. However, such a quick turn command may be created according to the present invention.

If the PreAct is STOP at steps S372 to S373 and a user repeatedly clenches and releases the teeth, the moving direction of the wheelchair is changed from the forward to the reverse or from the reverse to the forward direction at steps S374 to S380. If a user clenches and releases both side teeth one time, a clenching motion of the user after a predetermined time is deleted from a memory. It is very similar to distinguish a one click and a double click of a mouse.

As described above, if the control command generating unit 200 generates a command to control the wheelchair by recognizing a pattern of electromyogram signal, the display unit 230 displays the created command or outputs corresponding audio information. The display unit 230 may include a display panel for showing the created command and the recognized pattern, a control panel for setting threshold values for each channel to recognize a pattern and a memory for storing and reading the threshold values.

Figure 6:
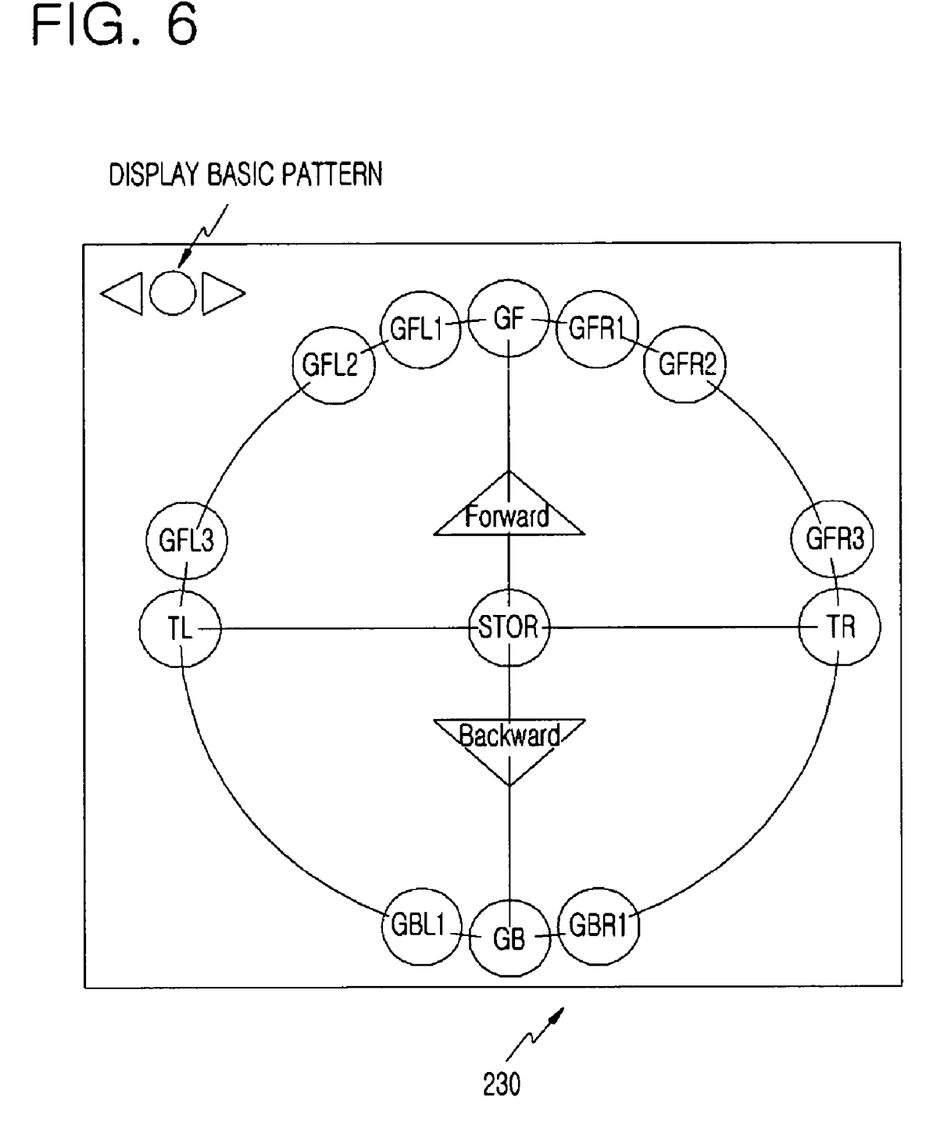
FIG. 6 shows a control panel of the vehicle controlling apparatus shown in FIG. 1 with control commands being displayed.

FIG. 6 shows a control panel of the vehicle controlling apparatus shown in FIG. 1 with control commands displayed.

Referring to FIG. 6 the display unit 230 displays a created wheelchair driving command. The display unit 230 also displays changes of moving directions and the recognized patterns.

Typical electric wheelchairs include an additional wheelchair driving unit 22 for driving the wheelchair. The wheelchair driving unit 220 drives the wheelchair by supplying a predetermined level of power according to commands inputted through a joy stick or various switches. The joy stick is generally used to input the commands. The joy stick supplies different levels of power to the wheelchair driving unit 220 according to the input command. The vehicle controlling apparatus according to the present invention includes the control command interface unit 210 for transferring a wheelchair driving command created by a teeth clenching motion because the vehicle controlling apparatus uses the teeth clenching motion as an inputting means instead of using the joy stick. The control command interface 210 converts the wheelchair control command to a predetermined level of voltage and the predetermined level of voltage is supplied to the wheelchair driving unit 220 to control the wheelchair according to the wheelchair control command.

As described above, the vehicle controlling apparatus and method according to the present invention allows a disabled person to conveniently control the wheelchair by embodying the vehicle controlling apparatus as a form of wearable headgear such as a hair-band or a hat and sensing the electromyogram signals generated from the temporalis muscle of the disabled person. Also, the vehicle controlling apparatus and method according to the present invention allows the disabled person to smoothly control the wheelchair by generating various driving commands based on the current teeth clenching pattern and the previous teeth clenching patterns.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. An apparatus for controlling a vehicle by a teeth clenching motion made by a user comprising:
   an electromyogram signal obtaining unit including electromyogram sensors disposed at both sides for generating an electromyogram signal according to a predetermined muscle moved when a disabled person clenches teeth, and a ground electrode connected to a body of the disabled persons for providing a reference voltage; and
   a vehicle driving unit including a control command generating unit for generating a vehicle driving command according to the electromyogram signal by classifying the electromyogram signal based on a side of teeth clenched, a duration time for clenching teeth and a sequence of teeth clenching motions made by the disabled person, a control command interface for generating a predetermined level of voltage according to the created vehicle driving command, and a vehicle driving unit for driving the vehicle according to the generated voltage,
   wherein the control command generating unit is configured to divide the electromyogram signal by a predetermined time;
   wherein the control command generating unit is configured to obtain a difference of absolute means value (DAMV) of each channel as feature value from the divided electromyogram signals obtained from two channels by DAMV=1 N−1 .times. i=2 N .times. .times. x .function. (i)−x .function. (i−1), where N denotes the number of samples in each of the divided electromyogram signals and x(i) represents the digital electromyogram signal value at an index i;
   wherein the control command generating unit is configured to classify the electromyogram signals into four basic patterns by comparing the obtained feature values of the electromyogram signals with a predetermined threshold value, classifying the electromyogram signals into an ON state if the feature value is greater than the predetermined threshold value and classifying the electromyogram signals into an OFF state if the feature value is smaller than the predetermined threshold value; and
   wherein the control command generating unit is configured to generate the vehicle driving command based on a classified pattern by setting a previous motion of vehicle as a reference value and analyzing the classified pattern based on the reference value.

2. The apparatus of claim 1, wherein the electromyogram signal obtaining unit further includes an amplifying/transmitting unit for amplifying the sensed electromyogram signal and transforming the amplified electromyogram signal to a digital signal, and the signal processing unit further includes a receiving/amplifying unit for receiving the electromyogram signal transferred from the electromyogram signal obtaining unit and amplifying the received signal.

3. The apparatus of claim 2, wherein the amplifying/transmitting unit includes a differential amplifying unit for calculating a voltage difference between the electromyogram sensors.

4. The apparatus of claim 2, wherein the electromyogram signal obtaining unit and the amplifying/transmitting unit are disposed at a fixing means including a hair-band and a hat.

5. The apparatus of claim 4, wherein the electromyogram sensors are fixed at the fixing means using an attachable/detachable member.

6. The apparatus of claim 1, wherein the control command generating unit further includes a display unit for displaying the command created by the control signal generating unit.

7. The apparatus of claim 1, wherein the electromyogram sensors are provided in plurality.

8. The apparatus of claim 7, wherein the electromyogram sensors are a right sensor and a left sensor, which are arranged about both temples that are used as a reference position for measuring brain waves varied according to teeth clenching, and the ground electrode is arranged at a center of a forehead for measuring a reference voltage.

9. A method for controlling a vehicle by a teeth clenching motion comprising the steps of:
   a) sensing an electromyogram signal of a predetermined muscle moved by a teeth clenching motion made by a user;
   b) generating a vehicle driving command according to the sensed electromyogram signal by classifying the sensed electromyogram signal based on a side of teeth clenched, a duration time for clenching teeth and a sequence of teeth clenching motions made by the user at a control command generating unit;
   c) generating a predetermined level of voltage according to the created vehicle driving command; and
   d) driving the vehicle according to the generated voltage,
   wherein step b) comprises the steps of:
     dividing the electromyogram signal by a predetermined time;
     obtaining a difference of absolute means value (DAMV) of each channel as feature value from the divided electromyogram signals obtained from two channels by DAMV=1 N−1 .times. i=2 N .times. .times. x function. (i)−x .function. (i−1), where N denotes the number of samples in each of the divided electromyogram signals and x(i) represents the digital electromyogram signal value at an index i;
     classifying the electromyogram signals into four basic patterns by comparing the obtained feature values of the electromyogram signals with a predetermined threshold value, classifying the electromyogram signals into an ON state if the feature value is greater than the predetermined threshold value and classifying the electromyogram signals into an OFF state if the feature value is smaller than the predetermined threshold value; and
     generating the vehicle driving command based on a classified pattern by setting a previous motion of vehicle as a reference value and analyzing the classified pattern based on the reference value.

10. The method of claim 9, further comprising the steps of: amplifying the sensed electromyogram signal and transforming the amplified signal to a digital signal at an amplifying/transmitting unit after the step a); and receiving and amplifying the transmitted electromyogram signal at a receiving/amplifying unit before performing the step b).

11. The method of claim 9, wherein in the step of generating the vehicle driving command when the vehicle is a stop state, the vehicle is controlled to make a left turn or a right turn if the vehicle driving command is generated by receiving the electromyogram signal transferred from one of channels, and the vehicle is controlled to move in a forward direction or a reverse direction if the vehicle driving command is generated by receiving the electromyogram signals from both channels for longer than a predetermined time.

12. The method of claim 11, wherein the moving direction are switched from the forward direction to the reverse direction or vice versa if the vehicle driving command is generated by receiving the electromyogram signals from both channel in two times.

13. The method of claim 9, wherein in the step of generating the command, the vehicle makes a turn to a corresponding side according to a vehicle driving command generated by receiving the electromyogram signal transferred from one of channels while moving in a forward direction.

14. The method of claim 13, wherein the vehicle makes a turn with a turning angle varied widely according to the number of commands transferred from each channel.

15. The method of claim 13, wherein the vehicle makes a turn with a maximum turning angle if the number of commands transferred from each channel is greater than a predetermined number or a time of inputting commands transferred from each channel is longer than a predetermined time.

16. The method of claim 13, wherein the vehicle makes a turn with a smaller turning angle than a current turning angle when the command transferred from each channel is a command to turn the vehicle to an opposite direction.

17. The method of any one of claims 13 and 16, wherein the vehicle makes a turn after receiving same commands for more than two blocks in order to prevent the vehicle be turned by error.

18. The method of claim 9, wherein the step of dividing the electromyogram signal includes the step of detecting loss contact in the electromyogram sensors and the ground electrode by determining whether maximum amplitudes are detected more than predetermined times from the signal obtained from the electromyogram sensor.

19. The method of claim 9, wherein a stop command is generated by converting the electromyogram signal to the digital signal, measuring a frequency of generating values identical to a maximum threshold and a minimum threshold value, and generating the stop command if the measured frequency is greater than a predetermined threshold value.

20. The method of claim 9, wherein the step b) includes the step of displaying the created command.

21. The method of claim 20, wherein the step of displaying the created command further includes the step of reproducing voice information denoting 'turn to left' or 'turn to right'.

* * * * *